US008605990B2

(12) United States Patent
Izumi

(10) Patent No.: US 8,605,990 B2
(45) Date of Patent: Dec. 10, 2013

(54) IMAGE RECOGNITION DEVICE AND IMAGE RECOGNITION METHOD

(75) Inventor: Kenji Izumi, Matsue (JP)

(73) Assignee: Shimane Prefectural Government, Matsue-Shi (JP)

( * ) Notice: Subject to any disclaimer, the term of this patent is extended or adjusted under 35 U.S.C. 154(b) by 548 days.

(21) Appl. No.: 12/734,912

(22) PCT Filed: Nov. 28, 2008

(86) PCT No.: PCT/JP2008/071608
§ 371 (c)(1),
(2), (4) Date: Jun. 2, 2010

(87) PCT Pub. No.: WO2009/072435
PCT Pub. Date: Jun. 11, 2009

(65) Prior Publication Data
US 2010/0246898 A1 Sep. 30, 2010

(30) Foreign Application Priority Data
Dec. 3, 2007 (JP) ................................. 2007-312819

(51) Int. Cl.
*G06K 9/00* (2006.01)
*G06T 15/00* (2011.01)
*H04N 5/225* (2006.01)
(52) U.S. Cl.
USPC ............ 382/154; 382/103; 345/419; 348/169
(58) Field of Classification Search
None
See application file for complete search history.

(56) References Cited

U.S. PATENT DOCUMENTS

| 7,167,575 B1* | 1/2007 | Nichani et al. ................ 382/103 |
| 7,920,718 B2* | 4/2011 | Marrion et al. ............... 382/103 |
| 2002/0085001 A1* | 7/2002 | Taylor ........................... 345/440 |
| 2002/0130951 A1 | 9/2002 | Kurono |
| 2004/0218784 A1* | 11/2004 | Nichani et al. ................ 382/103 |
| 2011/0013024 A1* | 1/2011 | Pryor ...................... 348/207.11 |
| 2012/0212630 A1* | 8/2012 | Pryor ........................ 348/207.1 |

FOREIGN PATENT DOCUMENTS

| JP | A-2001-38051 | 2/2001 |
| JP | A-2001-161665 | 6/2001 |
| JP | A-2002-277213 | 9/2002 |

(Continued)

OTHER PUBLICATIONS

International Preliminary Report on Patentability dated Aug. 12, 2010 for corresponding International Application No. PCT/JP2008/071608.

(Continued)

*Primary Examiner* — Randolph I Chu
(74) *Attorney, Agent, or Firm* — Oliff & Berridge, PLC

(57) ABSTRACT

The present invention is aimed at detecting an operator's height and position of each body part with a certain range of accuracy, which is used for calculation of a BMI value or operation of a game. An exercise assist device (101) is provided with a horizontal bar (102), a bar support (103) to support the bar, and a floor mat (104) on a surface of its body. A video camera (201) is mounted on the top of a monitor (701) as illustrated, for example, in FIG. 7 and captures the operator as well as the horizontal bar (102) and bar support (103) in one image. Since the horizontal bar (102) and bar support (103) together with the operator are captured in one image, they become a three-dimensional measurement reference, so that the operator's height can be calculated from the captured image.

6 Claims, 21 Drawing Sheets

(56) References Cited

FOREIGN PATENT DOCUMENTS

| JP | A-2003-28614 | 1/2003 |
| JP | A-2003-111867 | 4/2003 |
| JP | A-2005-23498 | 1/2005 |
| JP | A-2005-164448 | 6/2005 |
| JP | A-2005-164513 | 6/2005 |

OTHER PUBLICATIONS

International Search Report mailed on Jan. 20, 2009 in corresponding International Application No. PCT/JP2008/071608.

* cited by examiner

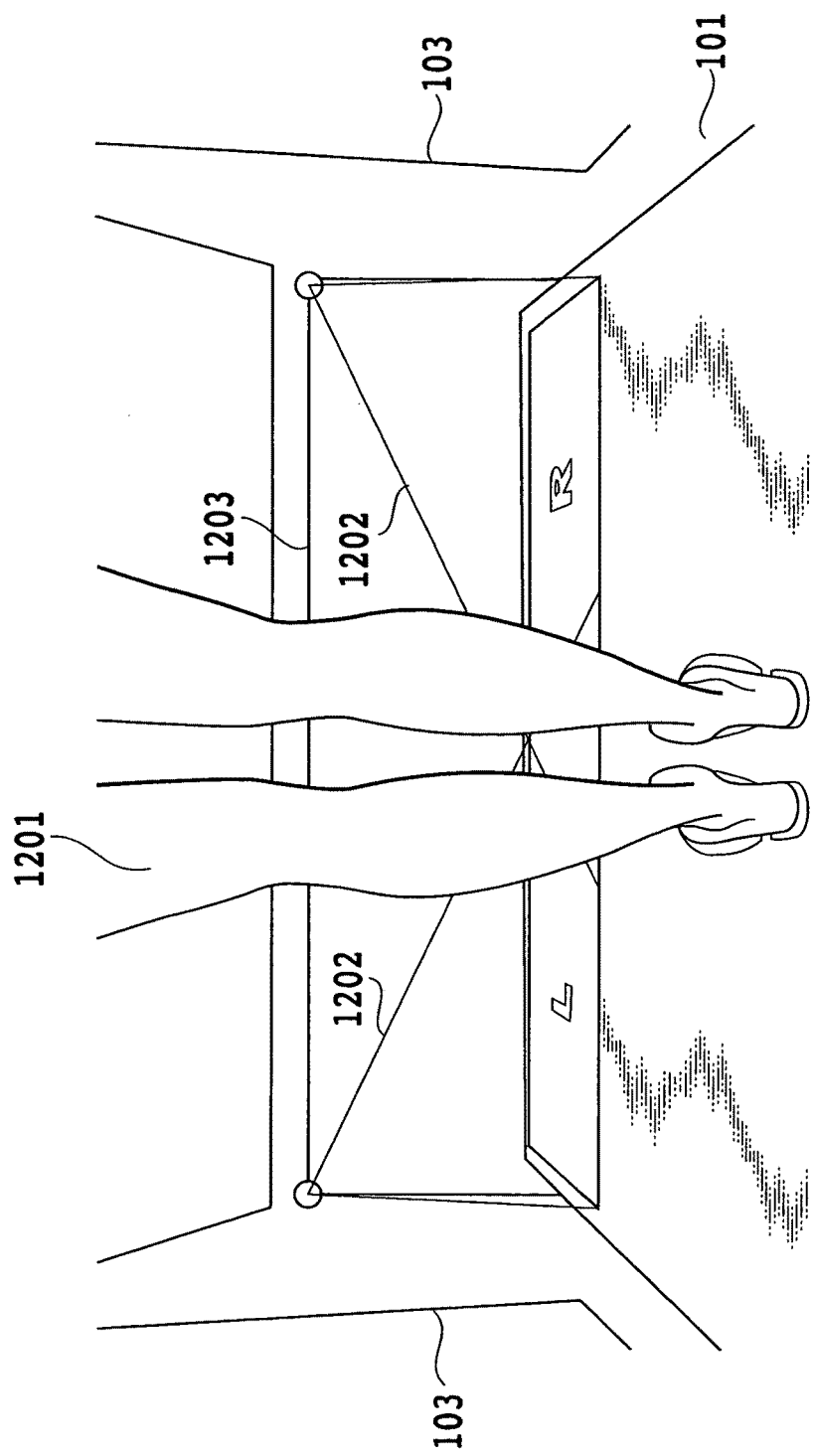

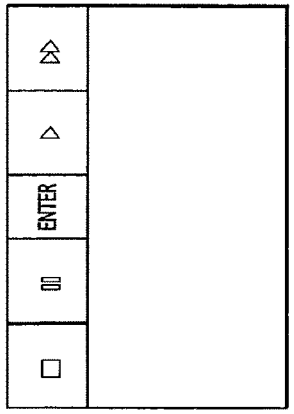
FIG.15C VIDEO CONTENTS
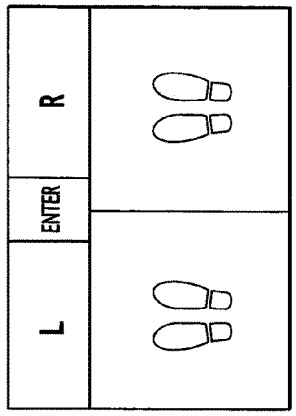
FIG.15F MULTI USER CASE 2
FIG.15B BASIC FORM EXAMPLE AT START
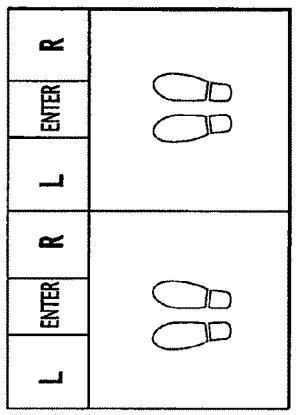
FIG.15E MULTI USER CASE 1
FIG.15A CASE WITHOUT LIGHTING (USE WHITE MAT OR MATERIAL WITH HIGH REFLECTIVITY)
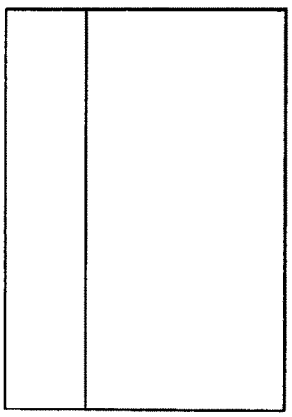
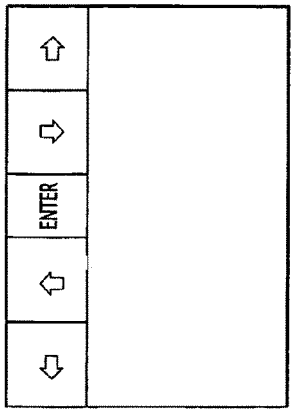
FIG.15D LEFT, RIGHT, TOP AND BOTTOM MOVEMENT MENU

IMAGE RECOGNITION DEVICE AND IMAGE RECOGNITION METHOD

TECHNICAL FIELD

The present invention relates to an image recognition device and an image recognition method, and more particularly, to an image recognition device and an image recognition method to measure an object to be measured on the basis of an image captured by a video camera and the like.

BACKGROUND ART

Recently, people have been health-conscious and various exercise assist devices have been developed in recent years. Meanwhile, metabolic syndrome has been highlighted as a potential risk to cause adult illnesses and the body-mass index (BMI) value has been emphasized as its reference value. The BMI value is the index that is calculated based on the relationship between body weight and body height and indicates the degree of obesity. When the body height is t (m) and body weight is w (kg), BMI is represented by the equation BMI=w/t2. An operator doing exercise with the use of the aforementioned exercise assist device measures his/her body weight and height after exercise, calculates the BMI value and observes an effect of exercise. It is useful if the operator can easily measure his/her body height and the like during exercise or between exercises.

In addition to increase of the number of game devices, the number of game devices an operator plays while using his/her whole body for improved user-friendliness and entertainment has also been increasing. In such game devices, if a computer can easily recognize the movement and position of the operator, various games corresponding to the movement and position of the operator can be produced.

In order to meet a need to obtain such a position of an object and spatial information, several methods have been proposed for general use, in which the position and movement of the object are detected by capturing an image of the object by a video camera and the like (see e.g. Patent Document 1). However, conventional position detection devices have a problem that they require calibration every shooting, installation work of their ancillary equipments, and a complicated work such as putting on and taking off a special marker to the object.

The present invention was made with the view of such a problem and an objective of the present invention is to provide an image recognition device and an image recognition method: in which an operator's height and the position of each body part of the operator are detected with a certain range of accuracy by a member that is an anthropometric reference provided on a floor mat of an exercise assist device or a game device and used for calculation of a BMI value and operation of a game.

Patent Document 1: Japanese Patent Laid-Open No. 2003-28614
Patent Document 2: Japanese Patent Laid-Open No. 2005-164448

DISCLOSURE OF THE INVENTION

In order to achieve such an objective, the invention is an image recognition device including: a floor mat sensor for generating different signals depending on a position where a foot placed; a three-dimensional measurement reference that is provided above the floor mat sensor and has more than or equal to four points to limit movement of the foot in a predetermined area; an imaging means being placed at a predetermined position relative to the three-dimensional measurement reference, for capturing an object to be measured on the floor mat and three-dimensional measurement reference in one image; an object position calculation means for extracting an image corresponding to the object to be measured and the three-dimensional measurement reference from the captured image and calculates a position of the object to be measured on the basis of a position information of the three-dimensional measurement reference that is previously obtained and stored and a distortion information relating to distortion of the image of the three-dimensional measurement reference captured by the imaging means; and an operation determination means for receiving the signal generated by the floor mat sensor and determines a predetermined operation depending on a position of the foot detected within the predetermined area; and an adjustment means for using a distance reference placed on the floor mat at a predetermined distance from the imaging means to adjust the position calculated by the object position calculation means on the basis of a distance between the object to be measured and the imaging means.

The invention may be configured such that the three-dimensional measurement reference has a marker on a surface thereof facing the imaging means so as to make extraction from the captured image easier.

The invention may be configured such that the three-dimensional measurement reference is a bar horizontally placed at a predetermined height above the floor mat sensor and has a space between it and the floor mat so that a portion of the foot can move in the predetermined area.

The invention may be configured such that when the three-dimensional measurement reference is captured by the imaging means, the captured image of the three-dimensional measurement reference has a rectangular shape.

The invention may be configured such that the distortion information is obtained by comparing the lengths of longitudinal and lateral sides and inclination of the image of the three-dimensional measurement reference captured by the imaging means with those of a reference image.

The invention is a method to recognize an image of an object to be measured on a floor mat having a floor mat sensor that generates different signals depending on a position where a foot is placed and a three-dimensional measurement reference that is provided above the floor mat sensor and has more than or equal to four points to limit movement of the foot in a predetermined area, the method including: an imaging step for capturing the object to be measured on the floor mat and the three-dimensional measurement reference in one image by an imaging means placed at a predetermined position relative to the three-dimensional measurement reference; an imaging means position calculation step for extracting an image corresponding to the object to be measured and the three-dimensional measurement reference from the captured image and to calculate a position of the object to be measured on the basis of a position information of the three-dimensional measurement reference that is previously obtained and stored and a distortion information relating to distortion of the image of the three-dimensional measurement reference captured by the imaging means; an operation determination step for receiving the signal generated by the floor mat sensor and to determine a predetermined operation depending on a position of the foot detected within the predetermined area; and an adjustment step for using a distance reference placed on the floor mat at a predetermined distance from the imaging means to adjust the position calculated by the object position calculation means on the basis of a distance between the object to be measured and the imaging means.

BRIEF DESCRIPTION OF THE DRAWINGS

FIG. 12 is a diagram illustrating a pattern projection method according to the present embodiment;

FIG. 15A is a diagram illustrating one example of a floor mat pattern projected according to one embodiment of the present invention;

FIG. 15B is a diagram illustrating one example of a floor mat pattern projected according to one embodiment of the present invention;

FIG. 15C is a diagram illustrating one example of a floor mat pattern projected according to one embodiment of the present invention;

FIG. 15D is a diagram illustrating one example of a floor mat pattern projected according to one embodiment of the present invention;

FIG. 15E is a diagram illustrating one example of a floor mat pattern projected according to one embodiment of the present invention;

FIG. 15F is a diagram illustrating one example of a floor mat pattern projected according to one embodiment of the present invention;

BEST MODE FOR CARRYING OUT THE INVENTION

Embodiments of the present invention will be described in detail and with reference to the accompanying drawings.

First Embodiment

Figure 1:
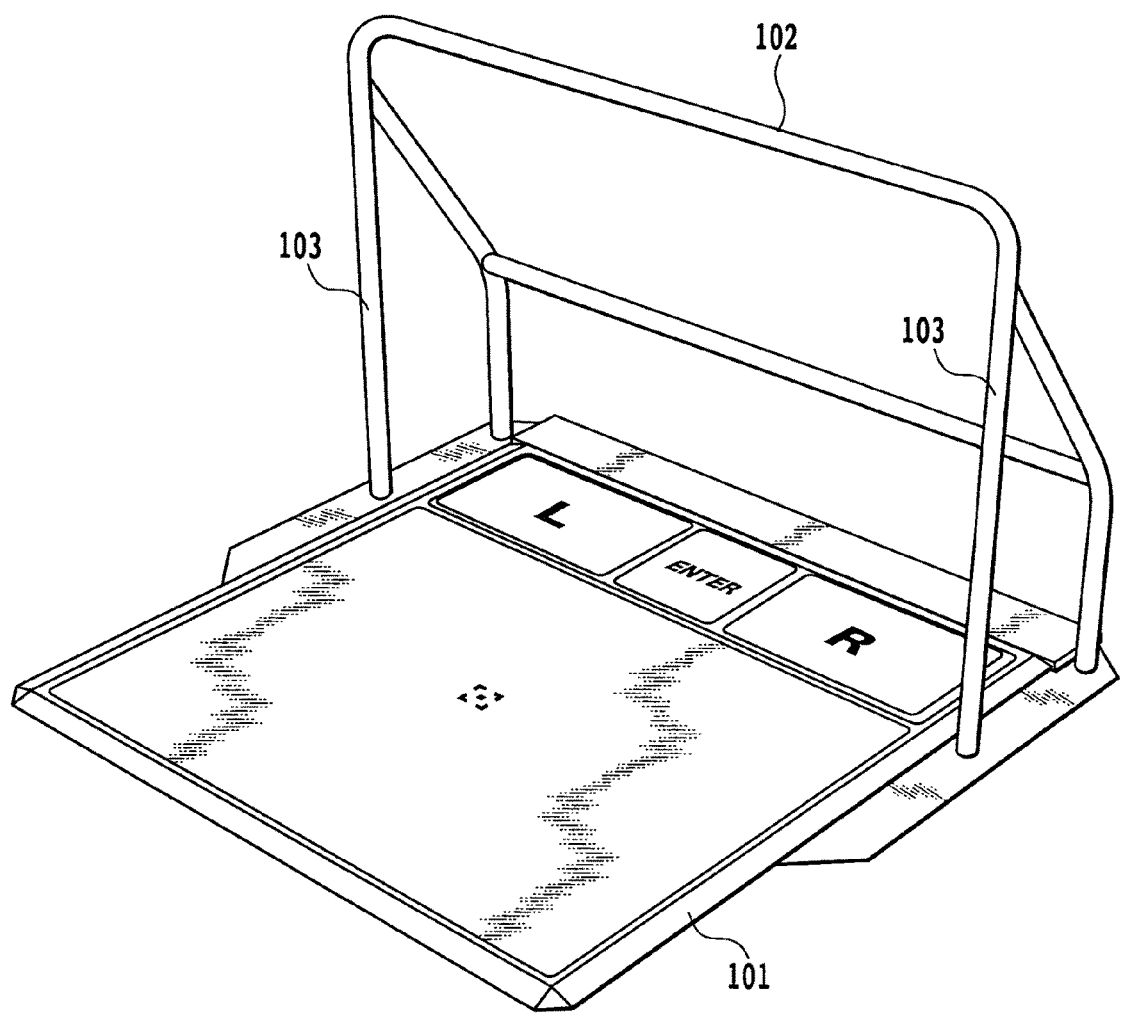
FIG. 1 is a diagram illustrating one example of an exercise assist device with a horizontal bar according to the present embodiment.
Figure 7:
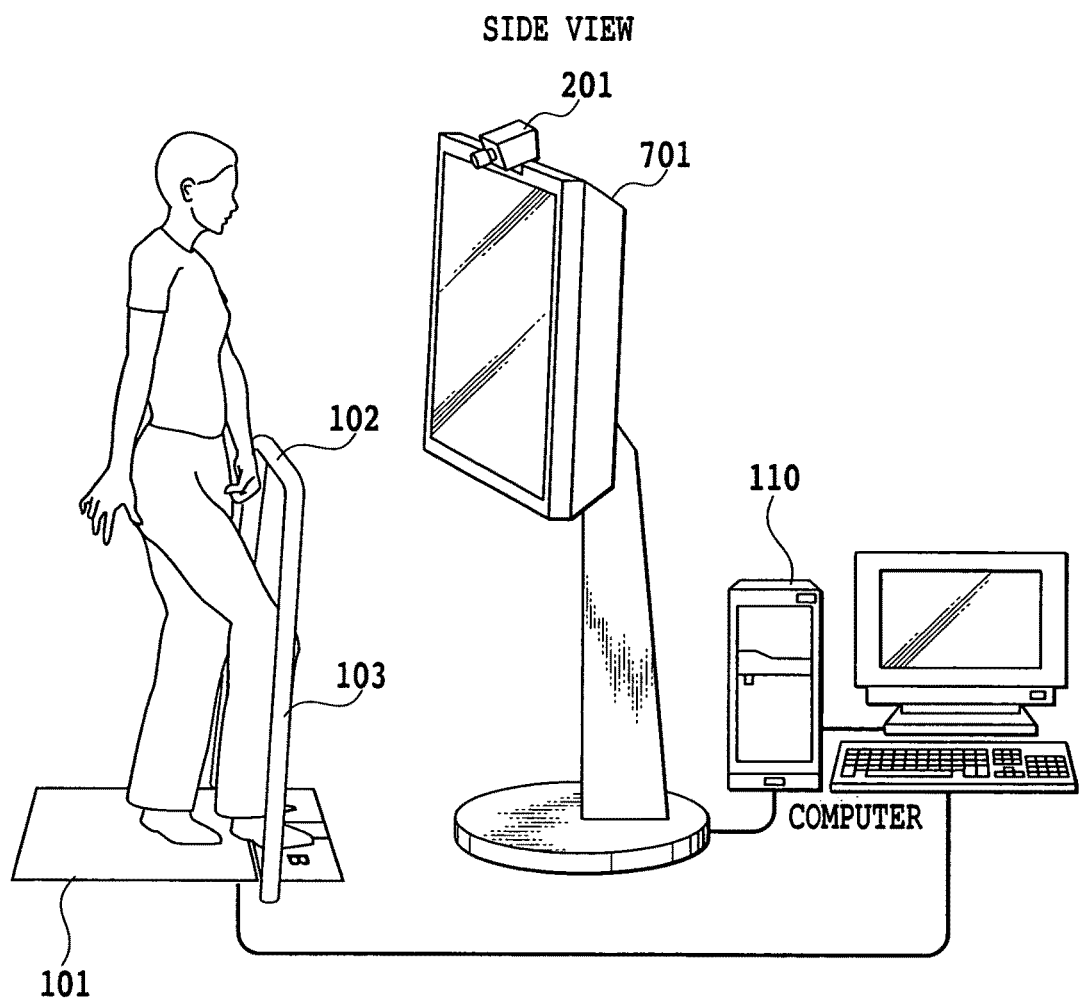
FIG. 7 is a diagram illustrating a scene where an operator pressurizes a floor mat with his/her foot according to one embodiment of the present invention.

FIG. 1 is a diagram illustrating one example of an exercise assist device with a horizontal bar according to the present embodiment, among an image recognition device illustrated in FIG. 7. An exercise assist device 101 according to the present embodiment includes a horizontal bar 102, a bar support 103 to support the horizontal bar 102, and a floor mat 104 provided on a surface of a body thereof. An operator does exercise or plays a game on the floor mat 104. Examples of exercise include jogging illustrated in FIGS. 18 and 19. The operator does exercise while watching a monitor 701. A video camera 201 and the like as an imaging means is provided on the top of the monitor 701, as illustrated in FIG. 7 and can capture the operator, horizontal bar 102 and bar support 103 in the same image. As described later, since the horizontal bar 102 and bar support 103 are captured together with the operator in the same image, they become a three-dimensional measurement reference, thereby enabling the height of the operator to be calculated from the captured image. According to the present embodiment, the video camera 201 is provided on the top of the monitor 701 in order to obtain the image and captures an image, but without limiting to this as long as a necessary image can be obtained; any imaging means known in this technical field such as an infrared camera can be used and installed at any location near the monitor. An infrared camera and a video camera may be integrated and used. In other words, for example, when an after-mentioned retro-reflective material is used as a marker, two types of cameras may be used in such a way that an infrared camera is used mainly for calibration of the three-dimensional reference and a normal video camera catches the movement of an operator.

A voice output device such as a speaker (not shown) is mounted on a system according to the present embodiment and can provide voice information relating to displayed contents and operation to the operator. In addition to displaying a workout menu as an image on a display, this function enables instructions and results to be informed by voice simultaneously, thereby informing GUI arrangement, which enables an operator with visual impairment to operate the device while holding the bar during a simple workout with less game property such as standing on one foot and walking.

Because the horizontal bar 102 and bar support 103 are provided on the front portion of the floor mat (on the side of the video camera and monitor), they do not disappear from an image due to the movement of the operator during capturing an image by the camera and therefore may be used as a stable measurement reference. Furthermore, the use of the horizontal bar 102 as a measurement reference, as the present embodiment, can make a distance between the operator and camera greater or equal to a certain distance and this distance can be always maintained, thereby avoiding troubles caused by being too close to the camera such as being incapable of capturing a whole image or focusing. In addition to this, using them with the floor mat can limit the position where the operator stands into a certain area, thereby making processing such as imaging and measuring easier. The measurement reference according to the present embodiment also enables measurement markers to be dispersedly arranged in a broad area, moderately and simultaneously on a captured screen, thereby allowing for a highly-reliable measurement. In addition to such an advantageous effect of the horizontal bar 102, a calibration system ensuring that the markers are always within an area capable of being imaged by the camera may be used therewith, thereby realizing a space-saving, multifunctional device and basically avoiding re-measurement every time after calibration at the time of initial installation.

Meanwhile, providing the horizontal bar 102 as the exercise assist device ensures the stable and secure movement of the operator such as an elderly operator in yoga exercise and rehabilitation training systems and also enables the operator to do workout while holding the bar.

Figure 20:
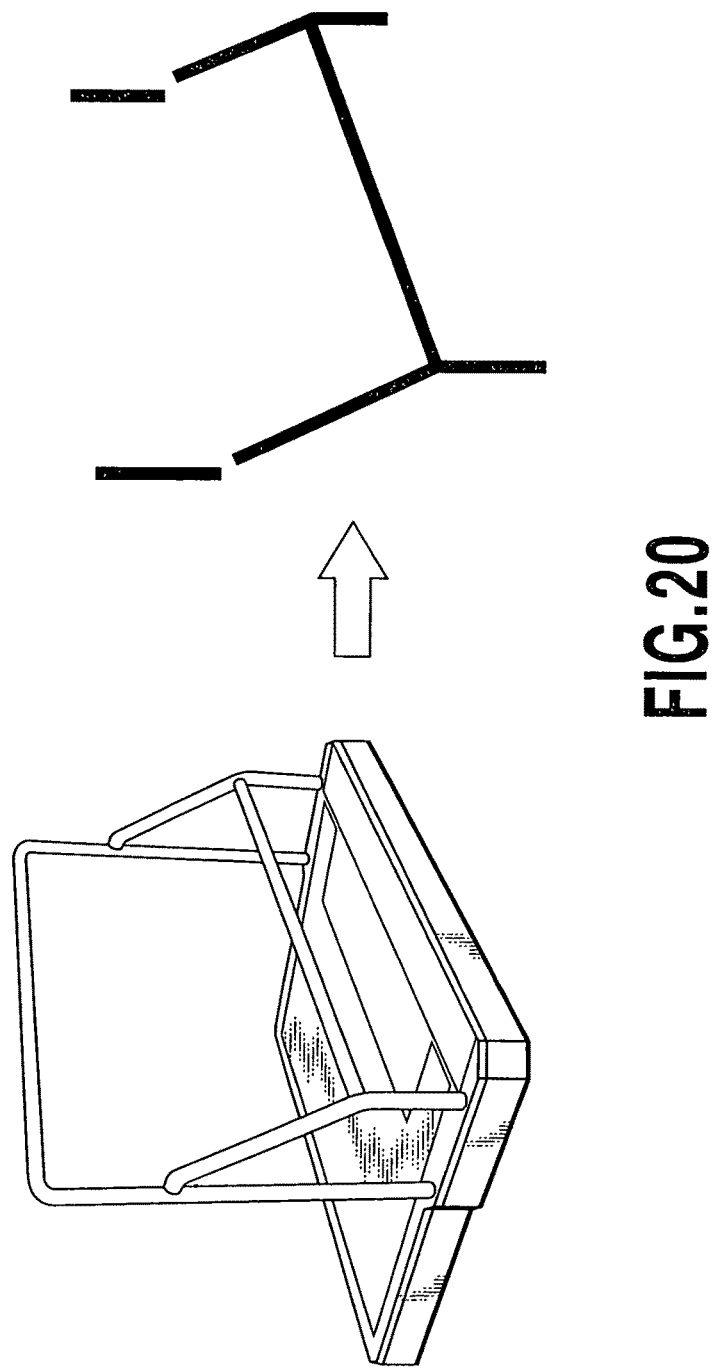
FIG. 20 is a diagram illustrating a marker according to one embodiment of the present invention.

The horizontal bar 102 and bar support 103 are captured by the video camera 201 to become the measurement reference as described above. To make this easier, as illustrated in FIG. 20, the markers are attached on the front surfaces (which are captured by the video camera 201) of the horizontal bar 102 and bar support 103 in order to make extraction easier after they have been read as an image. Various materials known in this technical field may be used as a marker material and usually a suitable material is selected depending on the camera to be used. For example, the normal camera requires distinctive coloring that stands out against a background color, and when an infrared camera is used, a retro-reflective material may be used. In this way, the marker can be used by attaching a suitable material to the bar and the like, but without limiting to this, the marker may be directly coated on the bar and any attaching method known in this technical field may be used. In the above description, the horizontal bar 102 and bar support 103 are used as the three-dimensional measurement reference, but without limiting to these, any member or structure can be used as the three-dimensional measurement reference. For example, the marker may be attached to the front surface of a pedestal of the exercise assist device 101 and used as the three-dimensional measurement reference or distance reference. According to the present embodiment, six markers are attached mainly to the corners and the like of the horizontal bar 102 and used as the measurement reference, but without limiting to this, at least any number more than or equal to four markers can be used, and instead of a dotted marker, a marker can be provided by drawing a line over the entire three-dimensional reference such as the horizontal bar 102.

Figure 2:
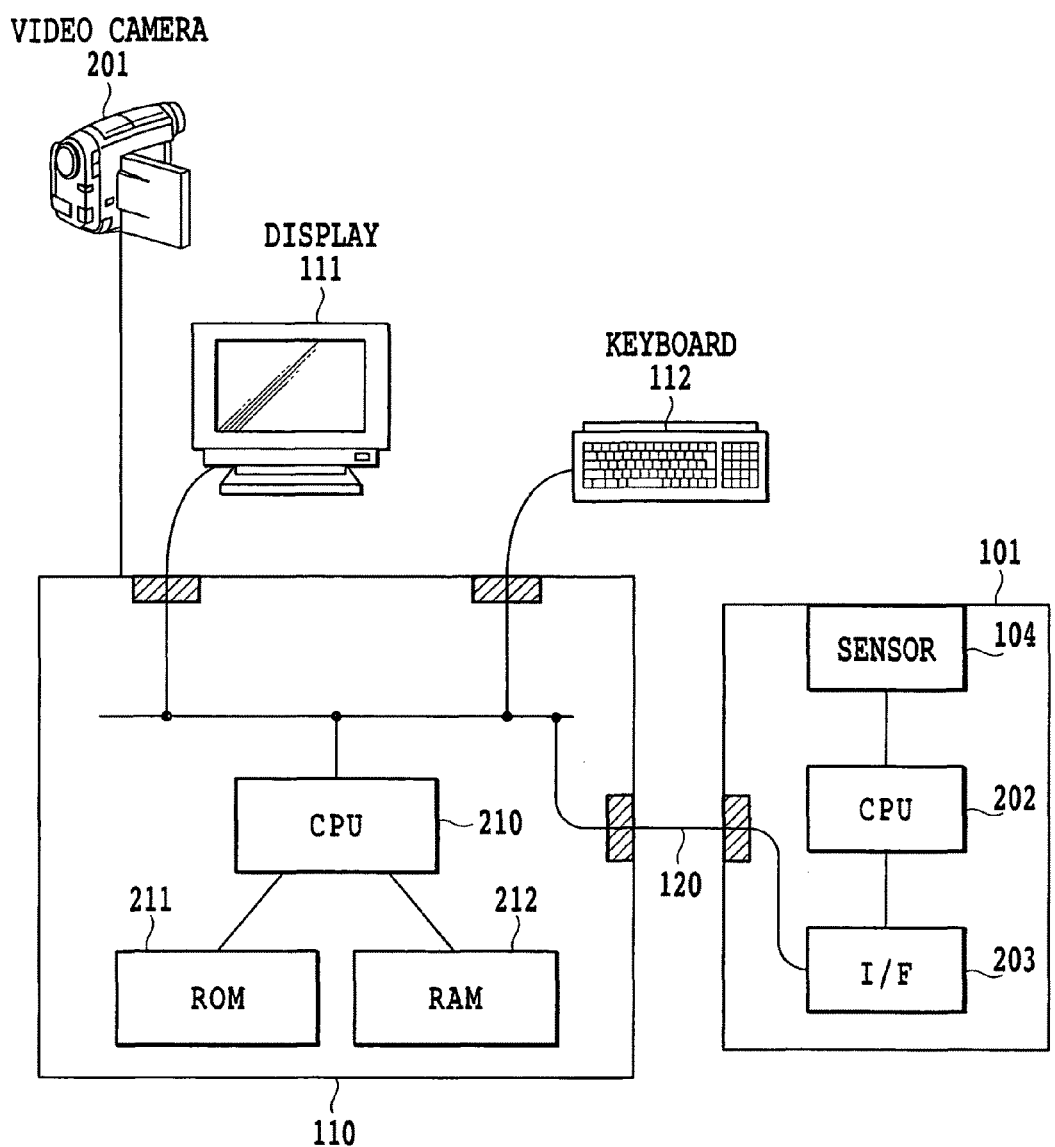
FIG. 2 is a block diagram schematically illustrating the structures of an exercise assist device 101 and a computer 110 according to the present embodiment.

FIG. 2 is a block diagram schematically illustrating a computer 110 of an image recognition device according to the present embodiment. A video camera 201, which is mounted on the top and the like of the monitor 701 and captures an image of the horizontal bar 102 and the like, is connected to the computer 110, and the captured image is taken into the computer 110. The captured image is subject to extraction of an image and calculation of a position, which are characteristics of the present embodiment, in the CPU 202; and anthropometric measurements are obtained from the calculated position to find a BMI value. The computer 110 generally includes the CPU 210, which executes a program stored in a ROM 211 and the like on a RAM 212 and outputs the result processed based on an image inputted from the image recognition device to a display 111 and the like.

Figure 5:
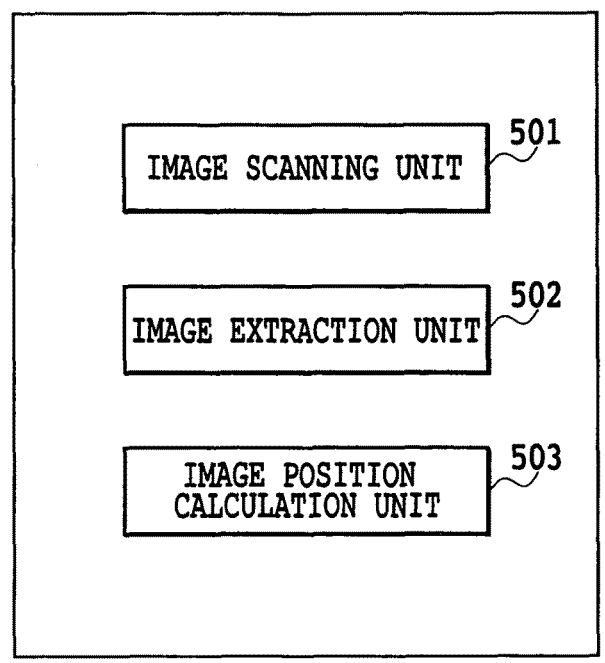
FIG. 5 is a block diagram illustrating one example of a functional module of a program processed within the CPU 202 in the exercise assist device 101 according to the present embodiment.

FIG. 5 is a block diagram illustrating one example of a functional module of a program processed within the CPU 202 in the image recognition device according to the present embodiment. As illustrated in FIG. 5, processing in the exercise assist device is performed at an image scanning unit 501, an image extracting unit 502 and an image position calculation unit 503. According to the present embodiment, processing from receiving an image from the video camera 201 to outputting data are performed at the three modules, but without limiting to this, more than or less than modules can be used for processing.

Processing According to the Present Embodiment

Figure 21:
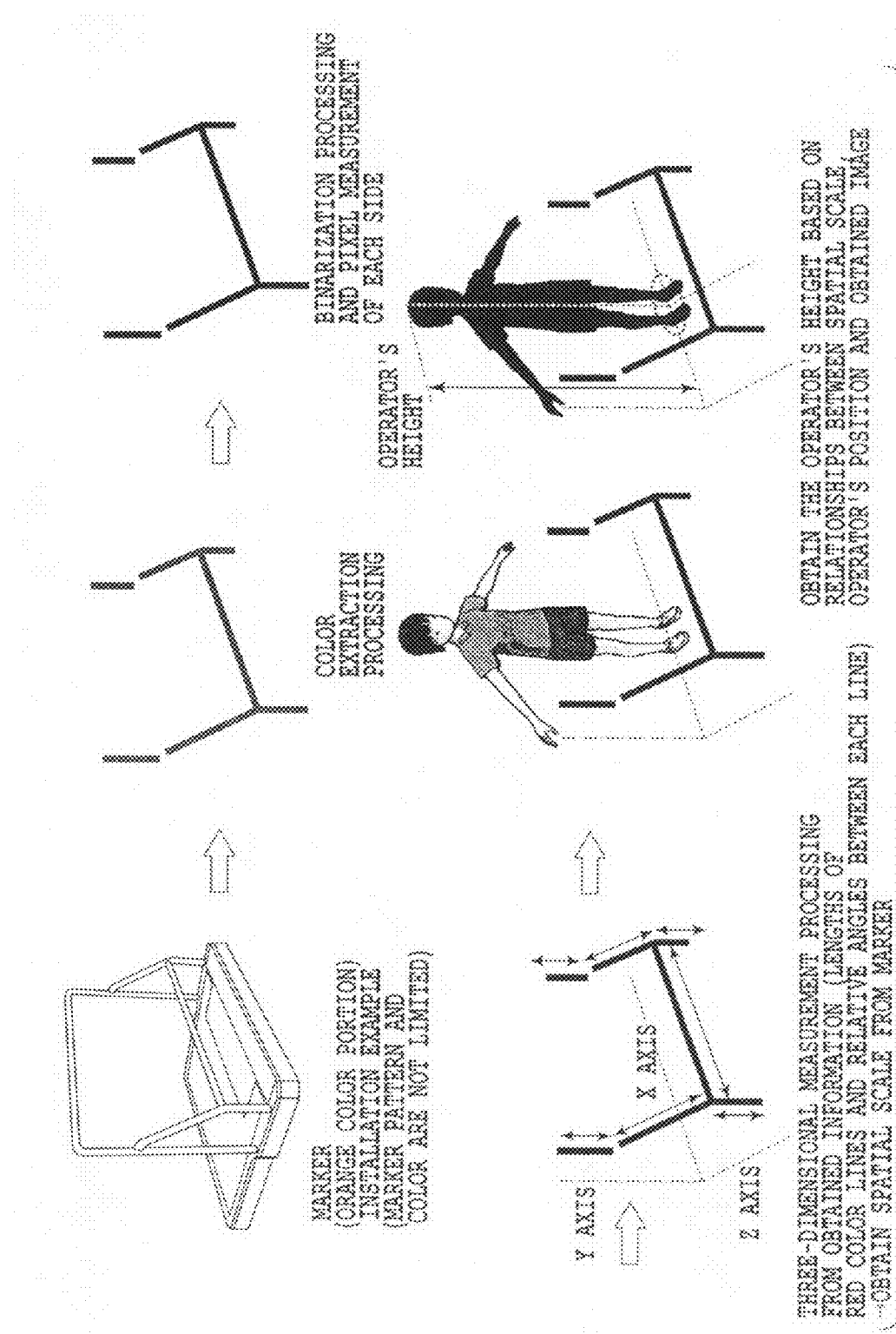
FIG. 21 is a diagram illustrating processing according to the present embodiment.

According to the present embodiment, as illustrated in FIG. 21, on the basis of the three-dimensional measurement reference such as the horizontal bar 102 captured by the video camera 201, processing to calculate the height of the operator, which is captured with the three-dimensional measurement reference, is performed.

FIG. 21 is a diagram illustrating processing of the present embodiment. Assuming that the image recognition device according to the present embodiment is newly installed, information such as distortion of a lens in the video camera 201 to be used and a distance between the marker attached to the horizontal bar 102 and the like and the lens must be inputted as an advance preparation. In addition, threshold setting and the like must be previously adjusted.

Next, for example in the case of a color image, at the image extracting unit 502, color areas predetermined as the marker are extracted from the three-dimensional measurement reference outputted at the image scanning unit 501, thereby extracting only an image of the three-dimensional measurement reference. Specifically, according to the present embodiment, an upper threshold and a lower threshold are set for each of a luminance signal Y and color difference signals U and V of a color NTSC signal and then pixels fulfilling all the thresholds are extracted.

After color extraction has finished, the image position calculation unit 503 binarizes the extracted marker portion to white and black and calculates the number of pixels composing longitudinal and lateral sides of the marker portion extracted from the image captured by the video camera 201. The lengths of the longitudinal and lateral sides and inclination of the captured image are compared with those of a reference image, thereby calculating distortion and scale of an imaging spacing. In addition to this, according to the present embodiment, when the distortion and scale are calculated, markers may be provided on more than or equal to 4 points and used as a reference. For example, if there are more than or equal to 4 reference points, these points can be connected to be line segments and calibration can be performed.

After such a preparation, actual measurement is performed, a relative relationship between the operator standing in the center of the exercise assist device 101 and the horizontal bar 102 is used to measure the operator's approximate height. In other words, by comparing the image of the operator with the image of three-dimensional measurement reference, the position of each body part and posture of the operator are determined on the basis of distortion information such as pre-calculated image distortion and scale. Although it is not described in detail here, the image of the operator is also extracted by any of methods known in this technical field. For example, there is a method in which the background of the operator is previously made distinctive, making extraction of the operator image easier.

As described above, according to the present embodiment, an image of the three-dimensional measurement reference such as the horizontal bar 102 as well as the operator captured by the video camera 201 is used to calculate the height of the operator. Thus, the operator can obtain his/her BMI value at real time anytime the operator wants to know while doing exercise on the exercise assist device 101. According to the present embodiment, although only the method to measure the body height is described in order to measure a BMI value, a body weight can be obtained by combining any conventional methods in order to find a BMI value.

As described above, the present embodiment enables the height of the operator to be automatically obtained and can be used for various applications other than this. For example, since the shape and position of each body part of the operator can be calculated with a fair degree of accuracy on the basis of their relationship relative to the three-dimensional measurement reference, measurement data of the operator other than his/her height can be easily obtained. Furthermore, since the operator's posture and movement of the each body part, such as hands, of the operator can be recognized, they can be applied to a game played using the whole body, thereby realizing mixed reality (MR). For example, the movement of the operator's head can be calculated and combined with the screen of the monitor 701, thereby implementing a heading game.

Second Embodiment

Here will be described an example according to the present embodiment. Basically in addition to a system structure of the aforementioned first embodiment, a floor mat sensor is used as a floor mat of the exercise assist device 101 and the exercise assist device 101 is used as a device for inputting data to the computer 110 and the like. Needless to say, an application example combined with the aforementioned first embodiment can also be implemented in the present embodiment. According to the present embodiment, the exercise assist device 101 has the floor mat 104 on the surface of the body thereof. When a predetermined area of the floor mat 104 is stepped on, the floor mat 104 outputs data corresponding to the stepped-on position. As described later, when the operator moves his/her foot, the horizontal bar 102 supports the operator and also limits the moving area of the operator thereby to limit the movement of the foot so as to allow for a stable data input by the foot.

Figure 10:
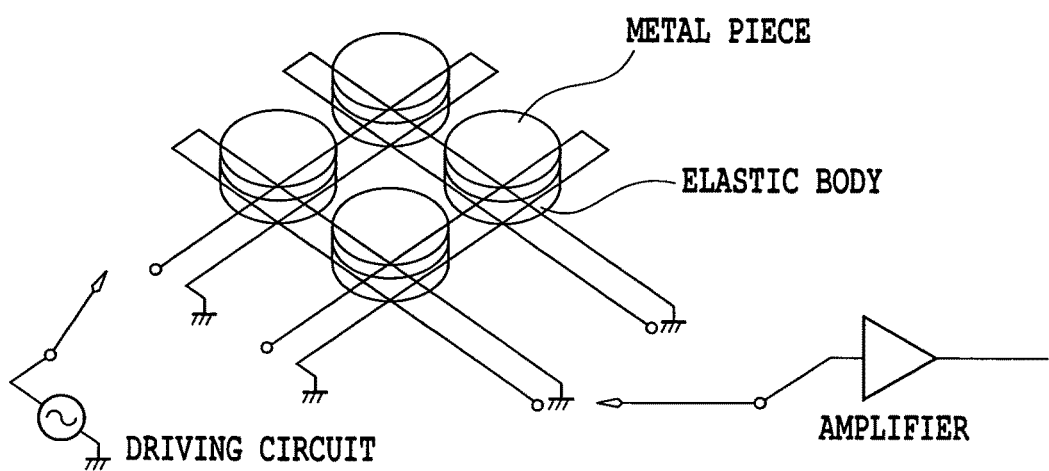
FIG. 10 is a diagram illustrating an example of a floor mat structure.

The exercise assist device 101 according to the present embodiment has the floor mat 104 attached on the surface thereof as illustrated in FIG. 10. As illustrated e.g. in FIG. 7, when pressure is applied to the floor mat 104 by stepping thereon, the floor mat 104 outputs a signal corresponding to the stepped-on position. FIG. 10 is a diagram illustrating an example of the structure of the floor mat. The floor mat according to the present embodiment utilizes an electromagnetic guidance pressure distribution sensor (see e.g. Patent Document 2) as illustrated in FIG. 10, but without limiting to this, any technique known in this technical field can be used.

For example, although a pressure sensor is used in a present embodiment, any technique such as an electrostatic sensor can be used as long as it can output a signal indicative of a position where a foot is placed.

Figure 6:
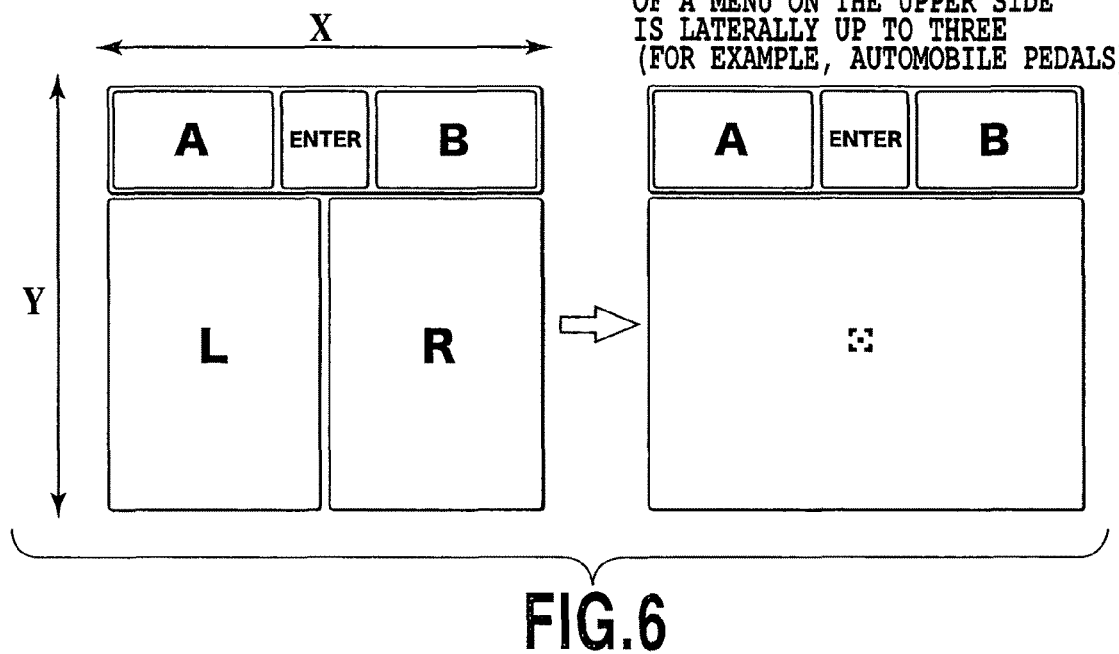
FIG. 6 is a diagram illustrating an example of a floor mat pattern according to one embodiment of the present invention.

A design indicative of input areas as illustrated in FIG. 6 are drawn on the surface of the floor mat and a waist-height bar extending horizontally is provided so as to separate "A" and "B" input areas from other areas. The operator holds the bar as a reference for the input areas and steps on an area indicative of a desired input, thereby outputting data corresponding to the stepped-on area. Specifically, FIG. 6 indicates an area for A input, an area for B input and an area indicative of ENTER, and stepping on each area enables data indicated by the area to be outputted. Alternatively, the operator can step on an information input area A or B first and then step on ENTER, thereby outputting data A or B that is first stepped on. In this way, according to the method of the invention of the present application, control can be performed so that the operator steps on the floor mat twice or more times to generate a pattern of a signal and data corresponding to the pattern is determined and outputted. Among these methods of the invention of the present application, a method to select two data as illustrated in FIG. 6 is relatively simple. For easier understanding, the present embodiment will be described using A and B.

Referring to FIG. 2 again, an outputted signal is processed and converted to data by information input which is a characteristic of the present embodiment, and the converted data is transmitted to the computer 110 via an interface 203. The computer 110 generally includes the CPU 210 which executes a program stored in the ROM 211 and the like on the RAM 212 and outputs the result processed on the basis of data inputted from the exercise assist device 101 to the display 111.

Figure 3:
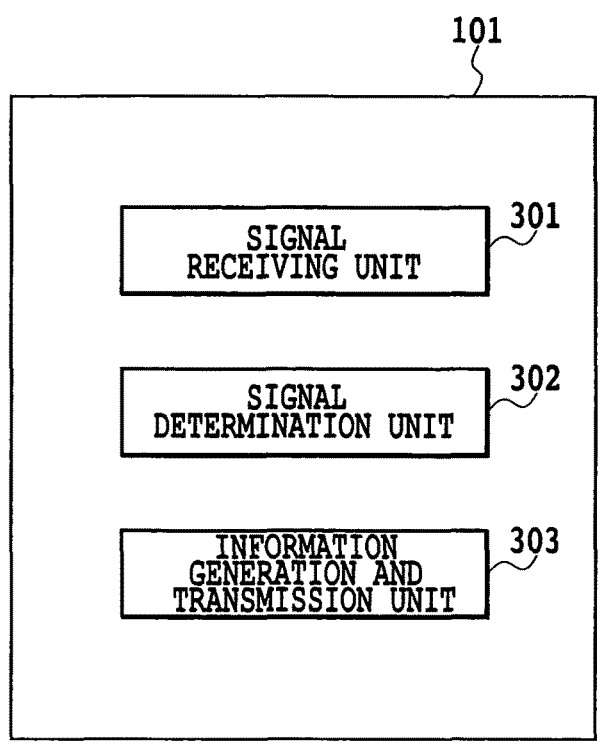
FIG. 3 is a block diagram illustrating one example of a functional module of a program processed within a CPU 202 in the exercise assist device 101 according to the present embodiment.

FIG. 3 is a block diagram illustrating one example of a functional module of a program processed within the CPU 202 in the exercise assist device 101 according to the present embodiment. As illustrated in FIG. 3, processing in the exercise assist device 101 is performed at a signal receiving unit 301, a signal determination unit 302 and an information generation and transmission unit 303. According to the present embodiment, the processing from receiving a signal from the floor mat to outputting data is performed at the three modules, but without limiting to this, the processing may be performed at more than or less than three modules.

Figure 4:
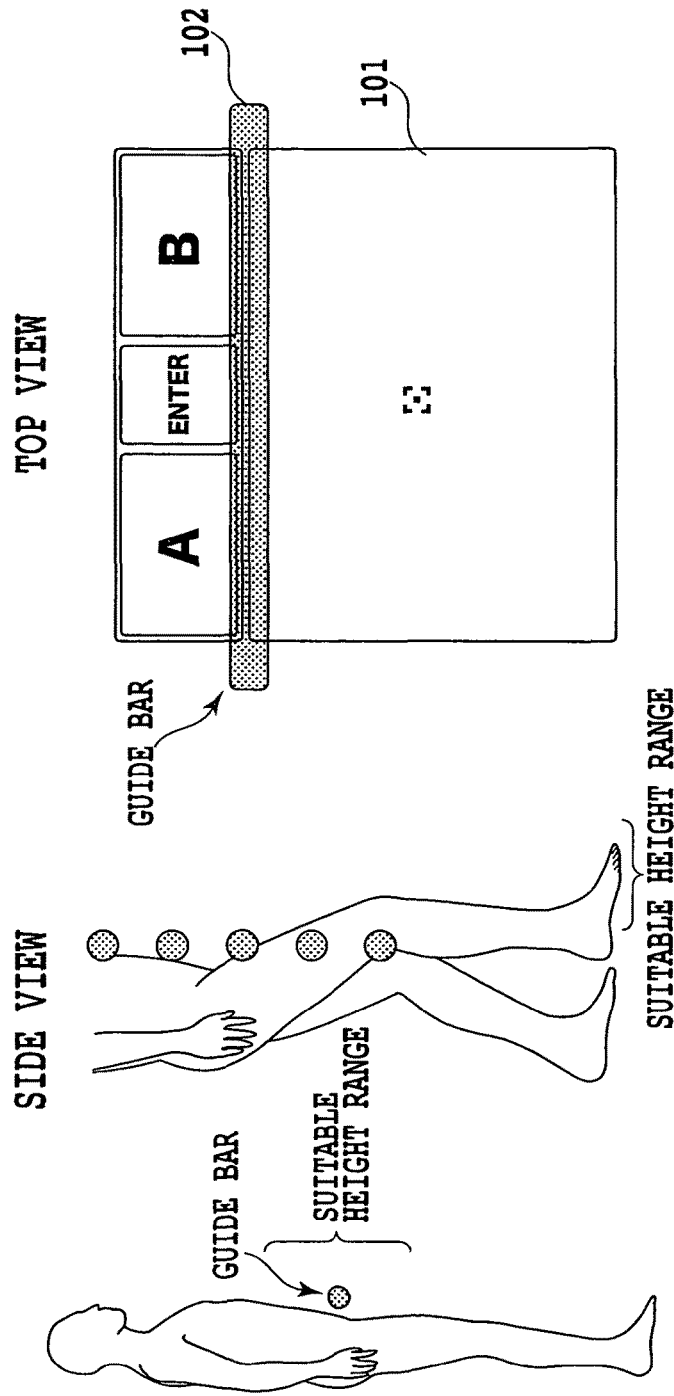
FIG. 4 is a diagram illustrating an installation position of the horizontal bar that is one example of a foot movement limiting means of the exercise assist device according to the present embodiment.
Figure 11:
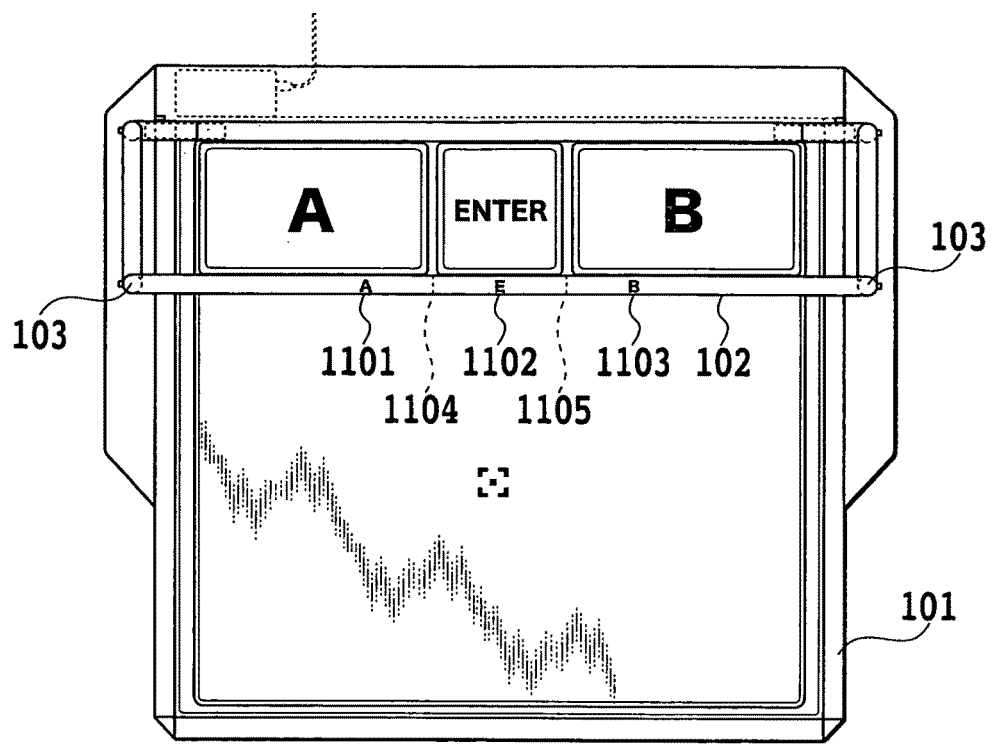
FIG. 11 is a diagram illustrating a case in which "A", "B" and "E" are shown in the horizontal bar of the floor mat according to one embodiment of the present invention.

FIG. 4 is a diagram illustrating a typical setting position of the bar. The horizontal bar 102, which is a foot movement limiting means according to the present embodiment, can be attached to the floor mat in various ways. In one example of the ways, as illustrated in FIG. 1, two bar supports 103 are provided at the lateral ends of the floor mat and the horizontal bar 102 is fixed between the supports 103 to make a space under the bar 102 for inserting a foot, thereby enabling the operator to accurately pressurize input areas such as "A" and "B" using the horizontal bar 102 as a reference. In other words, if there is an obstacle such as the horizontal bar 102, the operator at least ergonomically cannot step with both feet into an area where the movement of his/her body is limited (the area between the vicinity of an image of the horizontal bar 102 projected to the floor mat and the area opposite to the operator across the bar 102, i.e. input areas such as "A" and "B" in FIG. 7 or others). By this, unless the operator intentionally moves his/her foot into the area where the movement of his/her body is limited, the area is not stepped on; and therefore the prevention of incorrect input is expected. In this case, a border of the area where the movement of his/her body is limited is a line generated by projecting the horizontal bar 102 on the floor mat, as illustrated in FIG. 11. However, as described above, the projected line and border do not necessarily correspond to each other. That is, the border of the area where the movement of his/her body is limited may be on the opposite side or the same side of the operator and may be linear or curved and any border can be used depending on applications. For example, although the horizontal bar 102 limits the movement of the operator, it does not limit the movement of the operator so much around an area directly below the horizontal bar 102 and therefore the operator unintentionally may step on there with both feet. In such a case, it is effective to set input areas to the positions where the operator unintentionally cannot step on with both feet by placing the border farther apart from the operator (placing the border on the opposite side of the operator).

Furthermore, by setting the height of such a horizontal bar 102 to a suitable height, for example, between the chest and knees of the operator, when holding the horizontal bar 102 as a balustrade, the operator keeps some distance (the length of extended arm) from the balustrade. Accordingly, it is expected that the operator unintentionally does not step on the front area of the floor mat (input areas such as "A" and "B") unless the operator intentionally steps on there. By making the height of the bar variable (not shown), the position of the bar can be set at the height suitable to each operator.

According to the present embodiment, as describe above, the bar 102 is horizontally provided as the foot movement limiting means, thereby limiting the movement of the foot to a certain degree, preventing the areas other than the predetermined areas from being stepped on without checking with eyes and as a result reducing incorrect operation. In addition to this, the foot movement limiting means may be used as a reference of input areas. According to the present embodiment, such a horizontal bar 102 can prevent incorrect operation. In this way, the invention of the present application is characterized by providing a device such as the floor mat that adopts a foot input with a member or a unit to limit the movement of the foot. Such a member or unit is not limited to a configuration such as the horizontal bar 102 according to the present embodiment and variety of configurations may be used therefor. For example, a bar may be erected on the upper surface of the floor mat and used as the foot movement limiting means, or a portion of the upper surface of the floor mat may be mounded and used as the foot movement limiting means. Accordingly, the invention of the present application is characterized by setting input areas on the floor mat and providing an obstacle member to limit the movement of a foot, thereby preventing incorrect input and improving a man-machine interface.

The horizontal bar 102 may be one simple bar. Also, the bar 102 may be color-coded according to the design of the floor mat, permitting input with a foot by watching the horizontal bar without watching the input areas of the floor mat. Specifically, referring to e.g. FIG. 11, the portions of the horizontal bar 102 above "A" and "B" areas and "ENTER" area of the floor mat 101 are marked with "A" 1101, "B" 1103 and "E" 1102 or color-coded respectively, enabling the operator to operate the device with his/her foot while watching the screen in front of the operator without looking down at the floor mat. Instead of color-coding, a predetermined position of the horizontal bar 102 may be labeled in Braille or with concavity and convexity, or the feeling of surface of the predetermined portion may be different from other portion so that even a sight-impaired operator can recognize the input areas of the floor mat. For example, describing with reference to the example illustrated in FIG. 11, letter portions, "A" 1101, "B" 1103 and "E" 1102 and border portions 1104 and 1105 may be carved in relief or labeled in Braille next to the letter portions.

(Example of Special Control)

According to the present embodiment, when information is outputted on the basis of a signal outputted from the floor mat that has been pressurized by a foot, further control as will be described below can be performed for accurate operation.

Figure 9:
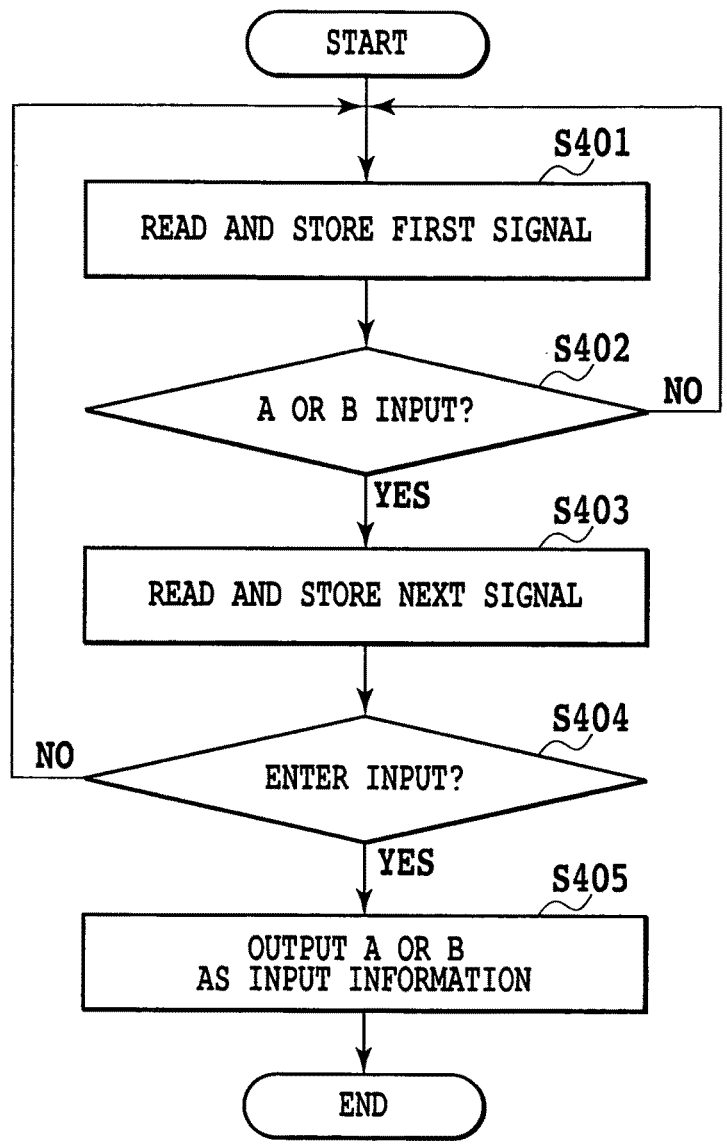
FIG. 9 is a flow chart illustrating processing of an information input method according to the present embodiment.

FIG. 9 is a flow chart illustrating processing according to the present example of control. Referring to FIGS. 3 and 6, the processing will be described based on the flow chart in FIG. 9. When any of areas of the floor mat illustrated in FIG. 6 is stepped on and any of signals is generated, the signal receiving unit 301 reads and stores a first signal (S401). For example if this inputted signal is a signal generated by stepping on the area "A" in FIG. 6, the signal is a signal indicative of information class "A". According to the present control processing and then a signal indicative of information class is first received from the floor mat, a signal indicative of information confirmation, which means confirming the first received signal, is received, and after that the first received signal indicative of information class is outputted, in this example, data A is outputted. Thus, since a first signal must be a signal indicative of information class, information cannot be outputted unless a signal indicative of information class A or B is received, for example, when the floor mat illustrated in FIG. 6 is used. Therefore, at step S402, the signal determination unit 302 determines whether or not the read signal was generated by stepping on the A or B area. If a signal indicative of information class (A or B of an example in FIG. 6) is first received, the signal receiving unit 301 reads the next inputted signal and the signal determination unit 302 determines whether or not a signal indicative of information confirmation (a signal indicative of ENTER of an example in FIG. 6) was received (S404). If it determines that a signal indicative of information confirmation was received, confirming that information of the first received information class was inputted, the information generation and transmission unit 303 generates and outputs the information corresponding to the input (S405).

By performing such special processing as described above, in the floor mat pattern illustrated in FIG. 6, when the A area is stepped on and then the ENTER area is stepped on, data indicating that the A area was definitely stepped on (for example, code such as "1" and "A") can be outputted, thereby reducing incorrect input with a foot, in addition to limiting the movement of the foot described above.

As described above, in the exercise assist device according to the invention of the present application, data input can be reliably performed using the floor mat. Considering normal use of the floor mat, it can be understood that this characteristic is more effective. In other words, since the operator normally stands to operate the floor mat and sometimes operates it while doing exercise, the floor mat is often used with a big-screen monitor as illustrated in FIG. 7 and is installed further apart from the screen in comparison with the case in which the operator sits to use the computer. In such a case, the operator tends to perform operation relying on his/her experience and memory while gazing the screen placed away from the operator and not so often watching buttons and a user interface near his/her feet. Even in such a case, using the exercise assist device according to the invention of the present application allows for reliable operation; and holding the horizontal bar 102 can stabilize the operator's posture. For example, in an example illustrated in FIG. 7, the operator performs operation using the floor mat 101 while watching the big screen monitor 701. In this example, since a decision button (ENTER in this example) is placed on the front portion of the center of the mat as illustrated in FIG. 6, the operator has only to move one step forward the center of the screen and does not need to look down for visual recognition each time.

Application of the present embodiment can eliminate a control box having a function such as start and reset which needs to be installed outside such as near the operator's foot or at hand in a conventional game mat or treadmill and the like. In other words, the conventional game mat or treadmill and the like requires the box for a switch and the like; however, by using an information input method according to the present embodiment, it is possible to input a plurality of required functions by combination of steps by foot, thereby eliminating the box. This has a cost reduction effect and also enables the operator to perform operation only by foot without the need to bend down for operating a switch or to operate another switch at hand.

By combining such a data input function of the present embodiment with the position detection according to the aforementioned first embodiment, the operator can perform a BMI measurement, for example, while selecting exercise according to an instruction from the floor mat.

Third Embodiment

According to the present embodiment, in addition to the aforementioned second embodiment, the floor mat can perform various types of processing on the basis of pressure information of the stepped-on position. In other words, since the floor mat according to the present embodiment uses an electromagnetic guidance pressure distribution sensor having a structure illustrated in FIG. 10, the exercise assist device according to the present embodiment performs various types of processing such as specifying the center of gravity of the operator on the floor mat on the basis of the outputted pressure information of each stepped-on position. The exercise assist device of the present embodiment has the same system structure as that of the first embodiment except that in the present embodiment the floor mat is limited to the pressure distribution sensor. According to the present embodiment, the floor mat can be used as a device for inputting various information such that, for example, as illustrated in FIG. 6, the front portion of the floor mat (areas marked with A and B) is used mainly for input such as A and B described relating to the first embodiment and the back potion thereof is used for other input and also can be used as the exercise assist device according to the aforementioned first embodiment. Furthermore, both areas are separated by the bar; and by using the bar as a reference the front side of the bar can be made to be the front portion.

In this example, a floor mat having the electromagnetic guidance pressure distribution sensor illustrated in FIG. 10 is used as the floor mat illustrated in FIG. 6, but without limiting to this any sensor can be used as long as it is a pressure sensor that can detect pressure distribution from the pressure applied by an object placed on the floor mat.

Figure 8:
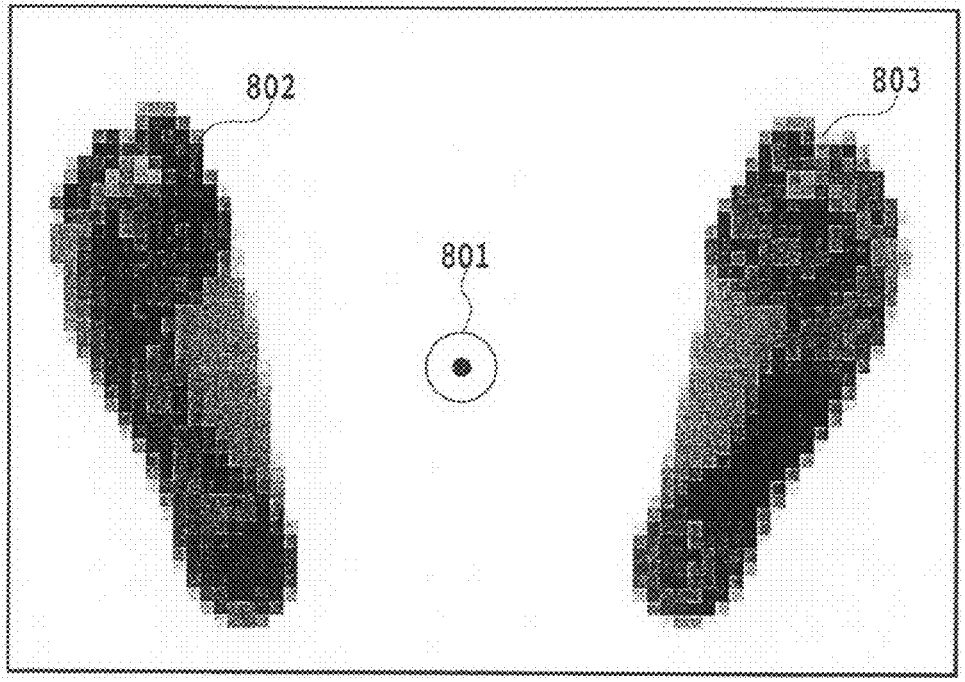
FIG. 8 is a diagram explaining a method for detecting a center of gravity according to one embodiment of the present invention.

In various information input devices using a floor mat, processing such as detecting the center of gravity of the operator is effective as described above. Since any detection method using pressure distribution of both feet known in this technical field can be used in order to detect the center of gravity, detailed description is skipped here. For example, as illustrated in FIG. 8, pressure distribution of both feet 802 and 803 is measured and then the position of center of gravity 801 is found based on the obtained distribution pattern. If the operator's position and his/her position of center of gravity are detected based on the pressure distribution of both feet, they can be applied to a game, for example, to an application in which characters within a display are moved by changing the position of center of gravity of the operator.

In the present embodiment, the center of gravity detected as described above is used to output more accurate information. In other words, in addition to the data determination method described relating to the first embodiment, the information input areas A, B and input confirmation area ENTER in FIG. 6 can output information only when the operator applies pressure with one foot. When the operator steps on the A or B area in order to select the area, the operator normally steps on with one foot and does not step on with both feet. Therefore, if information is inputted only when pressure is applied with one foot, more accurate information can be provided. In this case, by further adding a determining condition that the opposite foot of the foot placed on the information input area or input confirmation area (i.e., a pivoting foot) is stably placed on the back portion other than the information input area or input confirmation area and does not move, more accurate information can be provided. In this case, holding the bar makes the operator's body stable and the bar can be a reference for recognizing an operation area.

As described above, compared with the exercise assist device of the first embodiment only intending to input A or B, in the exercise assist device intending to be used for other purposes in addition to inputting A or B, it is more difficult for the operator to indicate the A or B area located in the front portion because the operator does not use only an area located in the front portion but often moves across the whole area of the floor mat. Therefore, when the floor mat is used as an input device of various information in the present embodiment, the method according to the invention of the present application is more effective.

Fourth Embodiment

The present embodiment is implemented basically with the same structure as those of the aforementioned second and third embodiments except that a portion of processing to determine what kind of information the operator attempts to output on the basis of a received signal is different from each other. That is, the exercise assist device or method according to the present embodiment, limits a time period from receiving a signal indicative of information class such as A or B to receiving a signal indicative of information confirmation and, if receiving the signal over a certain time period, the signal is disabled. Specifically, any method known in this technical field can be used; and as one example a first signal is received (step S401 in FIG. 9) and determined to be a signal indicative of information class (step S402 in FIG. 9), and then a timer is started and if the next signal is not received within a certain time period, for example 3 to 5 seconds, the processing is terminated. In this case, if a signal is received before the timer expires and it is determined that the received signal is not a signal indicative of information confirmation at step S404, the processing is also terminated. Alternatively, another signal may be waited until the timer expires.

According to the present embodiment, in processing to determine what kinds of information the operator attempts to output (steps S402 to S404 in FIG. 9), information is inputted only when a plurality of signals are received at the same interval of time, thereby further eliminating incorrect input in addition to the aforementioned embodiments.

Fifth Embodiment

The present embodiment is implemented basically with the same structure as those of the aforementioned second to fourth embodiments except that in the present embodiment the floor mat pattern is dynamically changed. In other words, in the exercise assist device or method according to the present embodiment the floor mat pattern such as A, B or ENTER is fixedly displayed by, for example, printing them on the floor mat whereas in the present embodiment the floor mat pattern is changed depending on status of use, thereby allowing for more effective information input. The floor mat pattern can be changed (i.e. displayed) by various methods; and the present embodiment uses a method in which a pattern is projected on the floor mat from above to display the floor mat pattern. This method will be described more specifically below.

FIG. 12 is a diagram illustrating a pattern projection method according to the present embodiment. The aftermentioned projection means for projecting a pattern such as an LED spot light and a liquid-crystal projector is attached to the bar support 103 and the like and performs projection on the floor mat. Then, a projection light 1202 can form a floor mat pattern on the floor mat. As illustrated in FIG. 12, if a projection unit is installed on the bar support 103 to obliquely perform projection, the operator's leg 1201 does not block out the projection, thereby avoiding the case in which the floor mat pattern is not well projected due to the shadow of the operator.

Figure 13A:
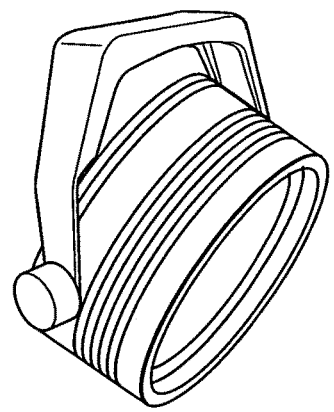
FIG. 13A is a diagram illustrating one example of a projection unit used according to the present embodiment.
Figure 13B:
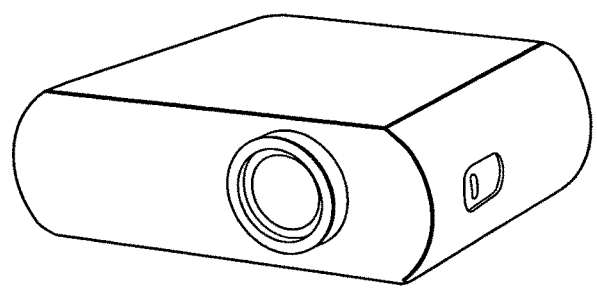
FIG. 13B is a diagram illustrating one example of a projection unit used according to the present embodiment.
Figure 14C:
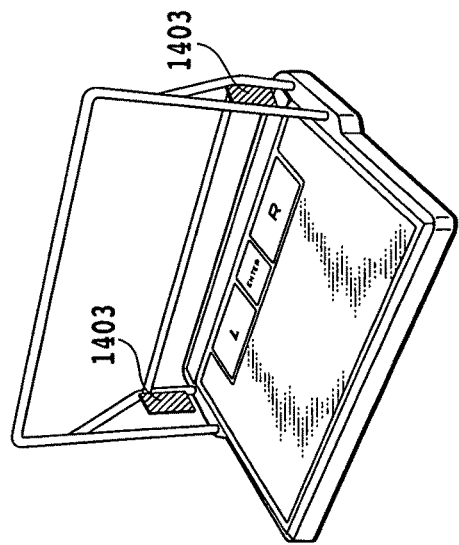
FIG. 14C is a diagram illustrating a case in which projection is performed laterally from both ends of a bar support.
Figure 14B:
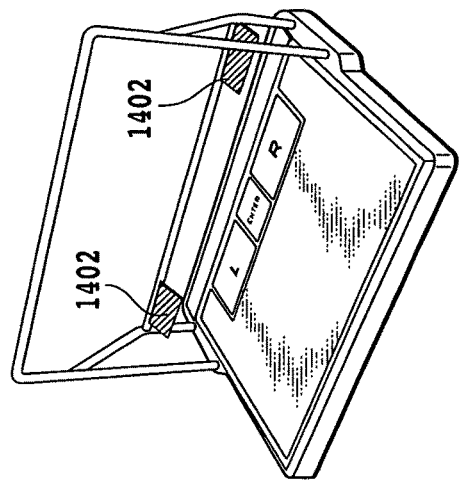
FIG. 14B is a diagram illustrating a case in which projection is performed obliquely from both ends of a bar support.
Figure 14A:
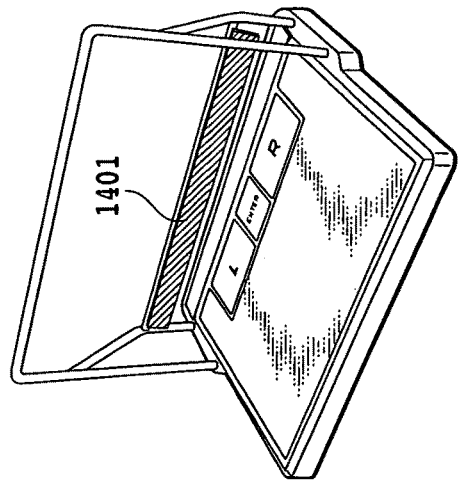
FIG. 14A is a diagram illustrating a case in which a unit is horizontally placed at a portion of a bar support.

FIGS. 13A and 13B are diagrams illustrating one example of a projection unit used in the present embodiment. FIG. 13A illustrates an example of a color LED spot light and FIG. 13B illustrates an example of an LED projector. According to the present embodiment, a unit as illustrated in FIGS. 13A and 13B is used as a projection unit, but various projection units known in this technical field may be used and other than projection units various units or members that can dynamically change the pattern may be used. These projection units must be installed on the device so that the shadow of the operator's leg does not block out the projection as described above. FIGS. 14A to 14C illustrate examples of the case in which a projection unit is installed on the device according to the present embodiment. FIG. 14A illustrates that a projection unit 1401 is horizontally installed on a portion of the bar support, FIG. 14B illustrates that a projection unit 1402 obliquely performs projection from the both ends of the bar support, and FIG. 14C illustrates that a projection unit 1403 performs projection from the lateral direction.

Since each of the projection units 1401, 1402 and 1403 illustrated in FIG. 14A to 14C is installed on the front portion of the device, the operator's leg hardly blocks the light. According to the present embodiment, L, R, ENTER, and others are projected by color-coding. Since it could be easily understood by a person skilled in the art that various patterns are possible with a projection unit; and setting and adjustment required to use the projection unit in this way, such as adjustment of distortion caused by an installation location, can be performed in a method known in this technical field, detailed description is skipped here. According to the present embodiment, a pattern is projected mainly on an area where the movement of the operator's body is limited, but without limiting to this, the projection unit can be used to project a pattern on the entire floor mat. According to the present embodiment, since a pattern is formed by projecting light, the pattern might be difficult to be seen when a strong light enters from outside. Therefore, it is effective to use an acrylic board 1203 or the like for shielding illustrated in FIG. 12.

The projection unit according to the present embodiment also can be connected to the computer 110 and various patterns can be transmitted from the computer 110 to be projected on the floor mat. FIGS. 15A to 15F are diagrams, each illustrating an example of the floor mat pattern projected in such a way. The device according to the present embodiment is also used in the situation where the operator is playing a game or doing exercise on the device of the present embodiment while watching the monitor illustrated in FIG. 7 and various patterns can be displayed and selected on the floor mat depending on content displayed on the monitor and content being performed at that time.

In order to change the floor mat patters in such a way, the surface of the floor mat is basically attached with any material usable in this technical field such as a plain material with high reflectance as illustrated in FIG. 15A so as to allow for the projection of the pattern. Using the aforementioned floor mat, various patterns are projected and floor mat patterns are formed. In FIG. 15B the most standard pattern, L and R, are used. FIG. 15C illustrates the case in which a video is displayed on the monitor and the operator can select playback, fast-forward and the like. FIG. 15D illustrates the case in which right, left, top and bottom can be indicated, similarly to FIG. 15C; and FIGS. 15E and 15F illustrate patterns that can be used by two operators. In the patterns of FIGS. 15E and 15F, two pairs of footprints are displayed to clarify that the device is being used by two operators when used by two operators, but are not essential (for example, such a situation may be displayed on the monitor). As described above, such a pattern may be formed by using the projection unit that projects a pattern on an area other than input areas.

Figure 16:
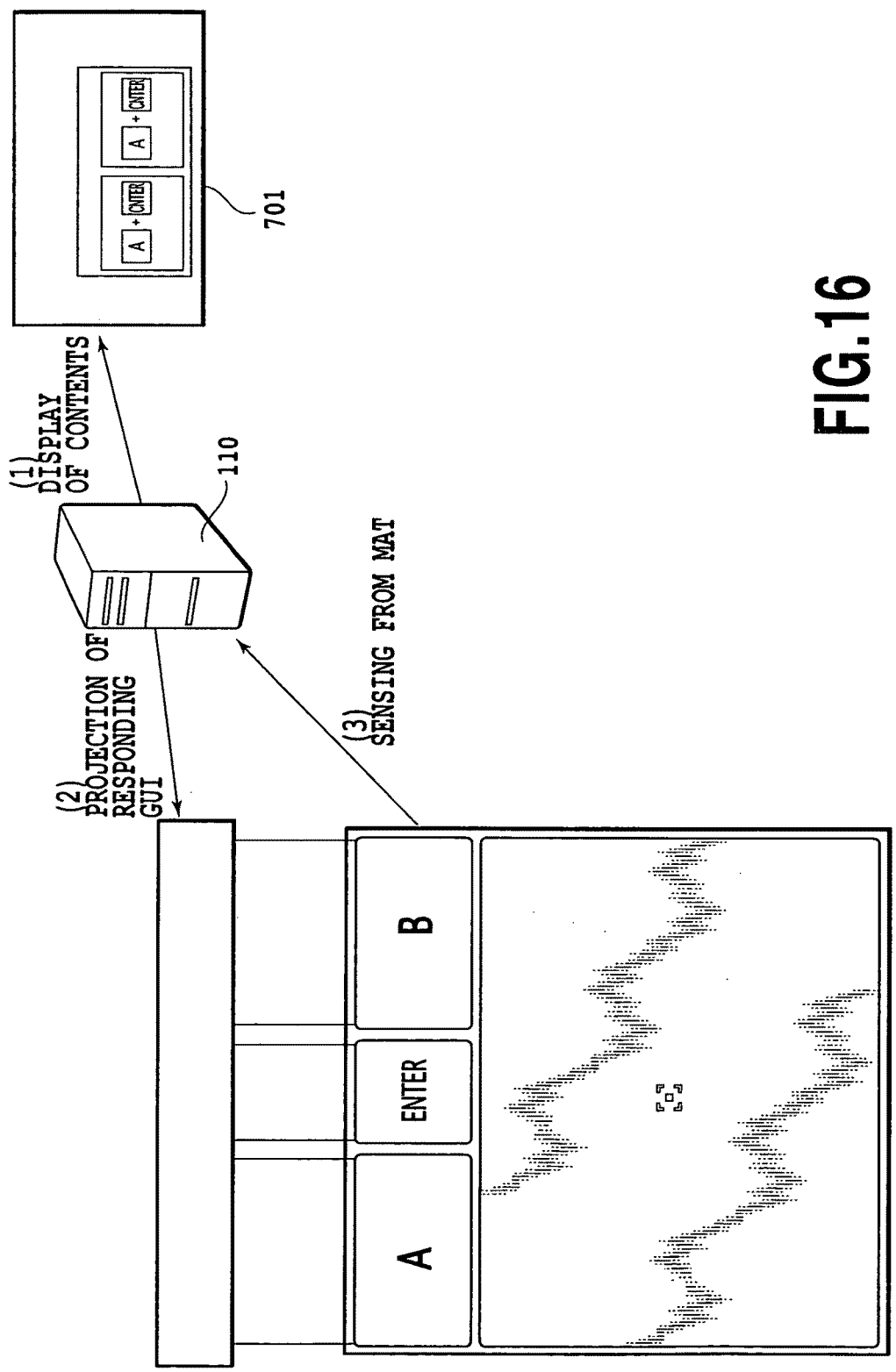
FIG. 16 is a diagram illustrating an application example of a variable floor mat pattern according to one embodiment of the present invention.
Figure 17:
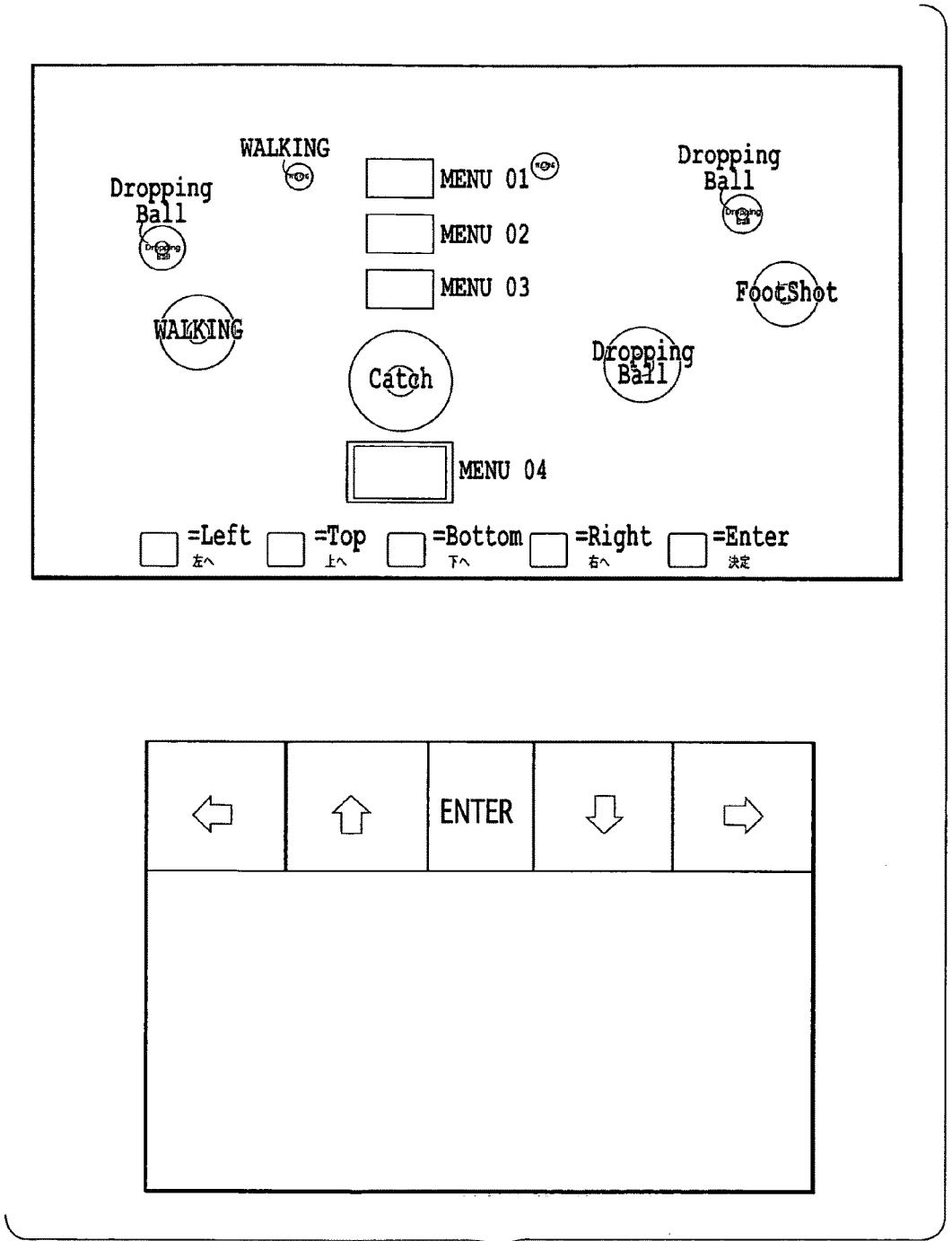
FIG. 17 is a diagram illustrating another application example of a variable floor mat pattern according to one embodiment of the present invention.

FIG. 16 is a diagram illustrating an application example of a variable floor mat pattern according to the present embodiment. This is a relatively orthodox application example in which when an input pattern is L and R at initial state, the monitor 701 displays switching the input pattern to A and B and accordingly the floor mat pattern is changed. As illustrated in FIG. 16, the computer 110 makes the monitor 701 display options A and B and instructs the projection unit to project a new floor mat pattern, A and B. When the operator steps on A or B while watching the monitor 701, information displayed on the stepped-on area is inputted to the computer 110, as described relating to the aforementioned first embodiment.

Figure 18:
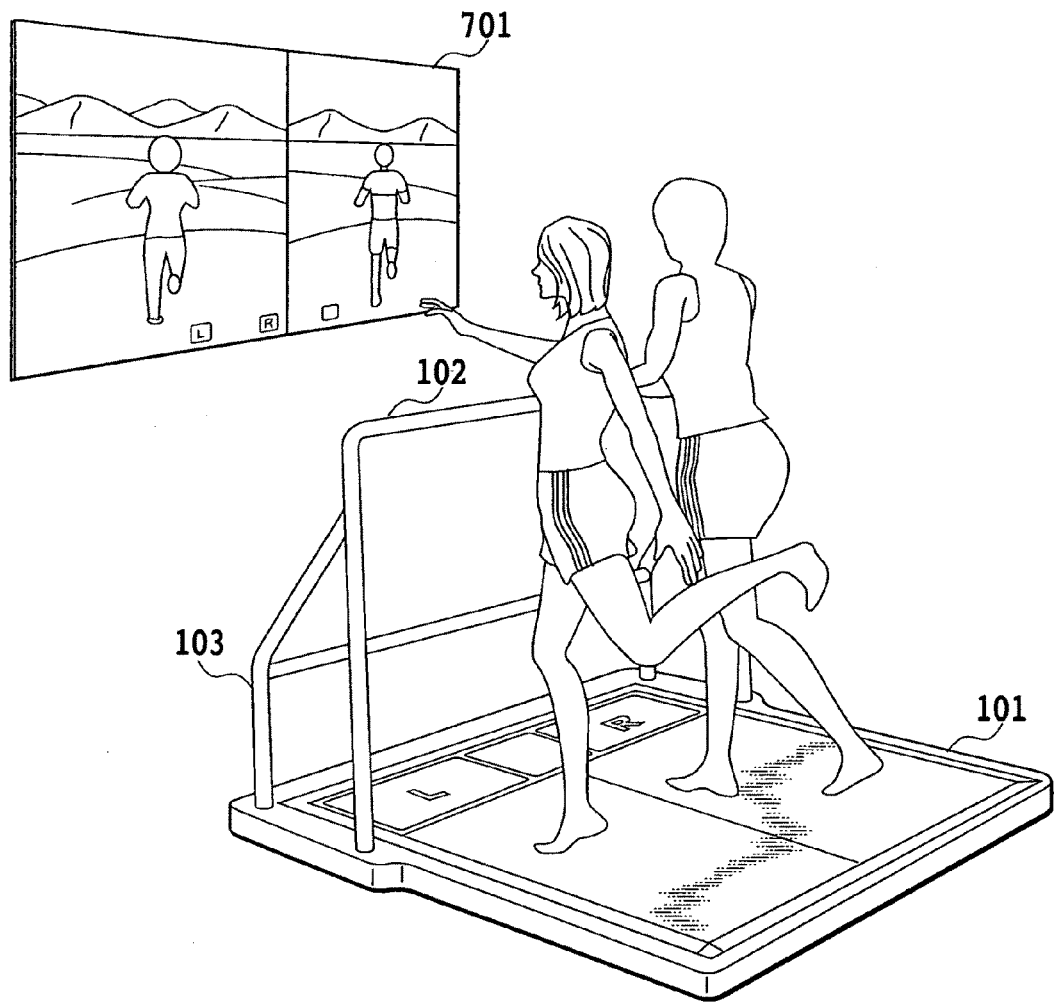
FIG. 18 is a diagram illustrating another application example of a variable floor mat pattern according to one embodiment of the present invention.
Figure 19:
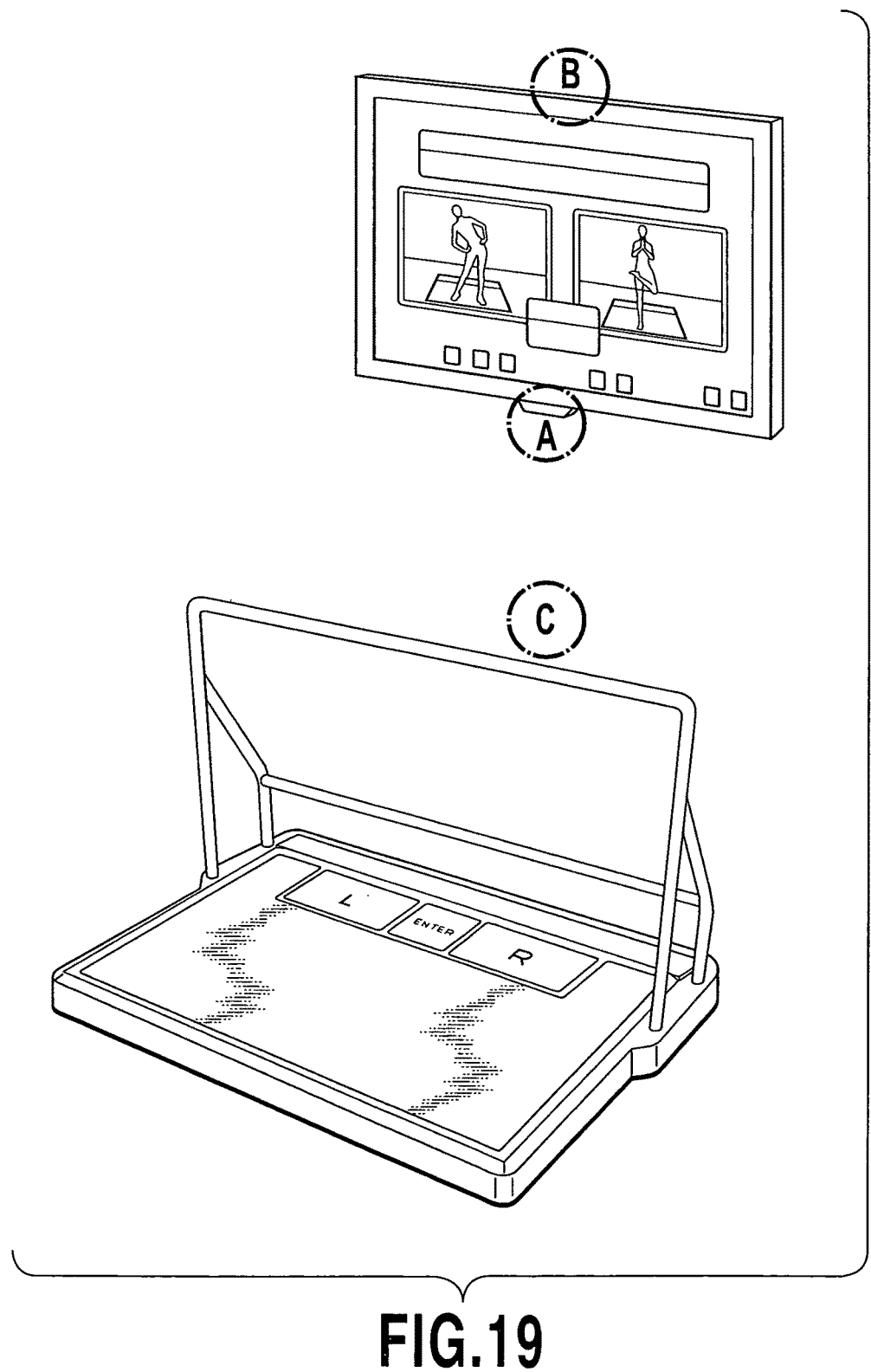
FIG. 19 is a diagram illustrating an application example of a variable floor mat pattern according to one embodiment of the present invention.

FIGS. 18 and 19 are diagrams illustrating other application examples of the variable floor mat pattern according to the present embodiment. With reference to FIG. 18, one type of game is displayed on the monitor 701 in which the input pattern L and R at initial state is changed to smaller area indications showing left, right, top and bottom by arrows on the monitor 701 and accordingly the floor mat pattern is changed. In FIG. 19, similarly, an instruction of exercise is displayed on the monitor 701 and when L or R is selected, the area near left foot or right foot of the operator is lighted up.

As described above, according to the present embodiment, the floor mat pattern can be changed variously according to the content, contributing to creation of more dynamic contents.

The invention claimed is:

1. An image recognition device comprising:
a floor mat sensor for generating different signals depending on a position where a foot placed;
a three-dimensional measurement reference that is provided above the floor mat sensor and has more than or equal to four points to limit movement of the foot in a predetermined area;
an imaging means being placed at a predetermined position relative to the three-dimensional measurement reference, for capturing an object to be measured on the floor mat and three-dimensional measurement reference in one image;

an object position calculation means for extracting an image corresponding to the object to be measured and the three-dimensional measurement reference from the captured image and calculates a position of the object to be measured on the basis of a position information of the three-dimensional measurement reference that is previously obtained and stored and a distortion information relating to distortion of the image of the three-dimensional measurement reference captured by the imaging means; and an operation determination means for receiving the signal generated by the floor mat sensor and determines a predetermined operation depending on a position of the foot detected within the predetermined area; and an adjustment means for using a distance reference placed on the floor mat at a predetermined distance from the imaging means to adjust the position calculated by the object position calculation means on the basis of a distance between the object to be measured and the imaging means.

2. The image recognition device according to claim 1 wherein the three-dimensional measurement reference has a marker on a surface thereof that faces the imaging means so as to make extraction from the captured image easier.

3. The image recognition device according to claim 1 wherein the three-dimensional measurement reference is a bar horizontally placed at a predetermined height above the floor mat sensor and has a space between it and the floor mat so that a portion of the foot can move into the predetermined area.

4. The image recognition device according to claim 1 wherein when the three-dimensional measurement reference is captured by the imaging means, the captured image of the three-dimensional measurement reference has a rectangular shape.

5. The image recognition device according to claim 4 wherein the distortion information is obtained by comparing the lengths of longitudinal and lateral sides and inclination of the three-dimensional measurement reference image captured by the imaging means with those of a reference image.

6. A method to recognize an image of an object to be measured on a floor mat having a floor mat sensor that generates different signals depending on a position where a foot is placed and a three-dimensional measurement reference that is provided above the floor mat sensor and has more than or equal to four points to limit movement of the foot in a predetermined area, the method comprising:

an imaging step for capturing the object to be measured on the floor mat and the three-dimensional measurement reference in one image by an imaging means placed at a predetermined position relative to the three-dimensional measurement reference;

an imaging means position calculation step for extracting an image corresponding to the object to be measured and the three-dimensional measurement reference from the captured image and to calculate a position of the object to be measured on the basis of a position information of the three-dimensional measurement reference that is previously obtained and stored and a distortion information relating to distortion of the image of the three-dimensional measurement reference captured by the imaging means; and an operation determination step for receiving the signal generated by the floor mat sensor and to determine a predetermined operation depending on a position of the foot detected within the predetermined area; and an adjustment step for using a distance reference placed on the floor mat at a predetermined distance from the imaging means to adjust the position calculated by the object position calculation means on the basis of a distance between the object to be measured and the imaging means.

* * * * *